United States Patent [19]

Felton, Jr. et al.

[11] 3,968,677

[45] July 13, 1976

[54] CONTINUOUS EVALUATION OF THERMAL STABILITY OF QUENCHING OILS

[75] Inventors: George F. Felton, Jr., Chadds Ford; Robert E. Royer, Chester, both of Pa.

[73] Assignee: Sun Oil Company of Pennsylvania, Philadelphia, Pa.

[22] Filed: Mar. 12, 1975

[21] Appl. No.: 557,718

[52] U.S. Cl. .................................... 73/15 R; 73/64
[51] Int. Cl.² ......................................... G01N 25/00
[58] Field of Search ............... 73/15 R, 53, 61.3, 64

[56] References Cited
UNITED STATES PATENTS

| | | | |
|---|---|---|---|
| 1,770,735 | 7/1930 | Funk | 73/60 |
| 3,680,356 | 8/1972 | Felton, Jr. | 73/15 |

FOREIGN PATENTS OR APPLICATIONS

| | | | |
|---|---|---|---|
| 1,138,708 | 7/1969 | United Kingdom | 73/15 |

*Primary Examiner*—Herbert Goldstein
*Attorney, Agent, or Firm*—J. Edward Hess; Donald R. Johnson; Anthony Potts, Jr.

[57] ABSTRACT

Testing apparatus and method for use in evaluating thermal stability of quenching oil wherein a relatively small quantity of the oil contacts a metallic heating element maintained at a temperature between about 1000°–1500°F. The contacting oil comes from a relatively large amount of oil and just prior to contact it is at a temperature lower than the flash point of the oil. Operation is continuous and substantially compresses testing time. Following the testing an oil sample can be chemically tested to determine its degree of degradation which is an indication of its thermal stability.

3 Claims, 1 Drawing Figure

U.S. Patent  July 13, 1976  3,968,677
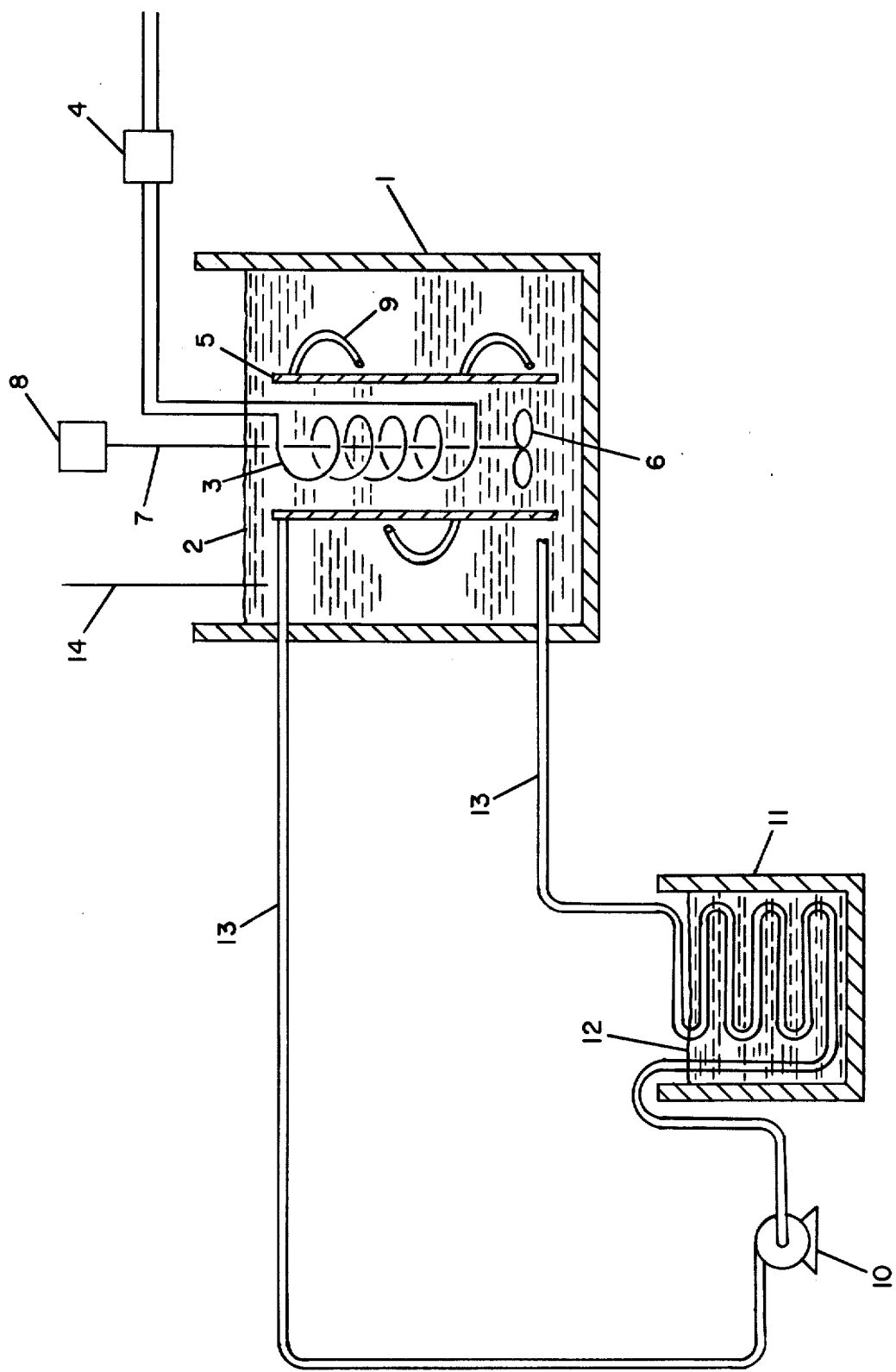

CONTINUOUS EVALUATION OF THERMAL STABILITY OF QUENCHING OILS

BACKGROUND OF THE INVENTION

The invention relates to an improved testing apparatus, and more particularly to an apparatus useful in evaluating the thermal stability of a thermal quenching oil (liquid hydrocarbon) under dynamic conditions. The invention also relates to a method of evaluating the thermal stability of a thermal quenching oil (liquid hydrocarbon) under dynamic conditions.

In the metalworking industries, it is common practice to use certain hydrocarbon liquids known as quenching oils for the purpose of quenching (i.e., controlled cooling) pieces of metal which have been heated to elevated temperatures to improve metallurgy. On the other hand, the repeated subjecting of the quenching oil to thermal shock (by the dipping thereinto of very hot pieces of metal) eventually causes degradation of the oil, with the formation of sludge, a marked increase in the viscosity of the oil, etc. It is important to the refiner and marketer of quenching oils to be able to quickly evaluate in the laboratory the thermal stability of the quenching oils he is offering for sale, so that he will know whether or not his products meet certain specifications.

An object of this invention is to provide a testing apparatus and method useful for dynamically evaluating the thermal stability of a liquid, and specifically of the quenching oil.

Another object is to provide testing apparatus of the aforementioned type and method which actually simulates the conditions involved in actual commercial use of a quenching oil, i.e., very hot metal immersed into a relatively large amount of oil having a temperature substantially lower than that of the hot metal.

Another object is to perform the testing in a relatively short period of time.

A further object is to provide a quenching oil testing apparatus which is simple in construction, easy to operate and repeatable.

A still further object is to provide a novel (laboratory) testing apparatus for quenching oils.

U.S. Pat. No. 3,680,356, issued Aug. 1, 1972 to George F. Felton, Jr., discloses a testing apparatus for use in evaluating the thermal stability of a quenching oil. However, to evaluate said stability by the disclosed apparatus requires weeks rather than days by the present invention. Furthermore the disclosed apparatus is subject to breakdown because of the relatively many moving parts. Also for safety reasons the temperature of the oil should not be allowed to exceed 300°–400°F because of the possibility of fire. This is a particular problem when the oil has a low flash point. The flash point of a typical conventional quench oil is about 320°–400°F.

SUMMARY OF THE INVENTION

The evaluation of the thermal stability of a liquid hydrocarbon quenching oil is determined in the following manner. A heating element located internally in a bath of the oil raises the temperature of the oil within the baffling means partially enclosing the heating element to about 1000°–1500°F. The volume of oil at this interface is small relative to the total volume of the bath. Mixing means provide forced circulation so that the heated oil is continuously mixed with the remaining cooler oil. The remaining oil, that is the oil outside the baffling means, is continuously cooled. Its temperature is maintained at a much lower temperature of about 100°–400°F. Because this apparatus simulates actual quenching conditions but substantially compresses the time requirements the apparatus and method provides a quick but accurate method of evaluating the thermal stability of such an oil. The stability of the oil is determined by periodic laboratory analysis samples of the used oil. The analysis includes pentane insolubles, viscosities, total acid number and other tests known to those skilled in this area of technology.

DESCRIPTION OF THE DRAWING

The accompanying FIGURE is a vertical section through one embodiment of an apparatus according to the invention.

DESCRIPTION OF THE INVENTION

A detailed description of the invention follows and is given in conjunction with the foregoing FIGURE.

Referring to the FIGURE, which illustrates one embodiment of the apparatus according to the invention, a suitable receptacle 1 contains a sample of the quenching oil 2 to be tested or evaluated. The combination serves as means providing a bath of a liquid hydrocarbon oil to be evaluated. The quenching oil 2 would ordinarily be a refined hydrocarbon product derived from crude petroleum and can contain suitable additives. Within the receptacle 1 and located entirely internally of said bath is a metallic element 3. In this embodiment the metallic member is illustrated as a coil; however, the shape of said member is not critical. Also said member can be, as shown, heated electrically; how the member is heated is not critical. Other means are equally satisfactory. The heat output of the metallic member 3 is controlled by a suitable device 4 which is connected to a power source, not shown. Partially enclosing the heated metallic member 3 is a baffling means such as a sleeve 5. The sleeve 5 neither extends to the surface of the oil 2 nor touches the bottom of the receptacle 1; therefore it partially encloses the metallic member. Thus the oil 2 can circulate freely inside the baffling means. The baffling means can contain holes or be entirely closed. It can be constructed of a suitable metal or ceramic or any material which does not chemically react with the oil 2 at room or at an elevated temperature. All of the surfaces contacting the oil are constructed of materials which do not chemically react with the oil at room or an elevated temperature. The baffling means is provided for safety reasons and to insure rapid fluid flow around the heated metallic member.

The temperature of the heated metallic member 3 is generally the temperature of the metal that is quenched. Thus normally the heated metallic member has a temperature range of about 1000°–1500°F; the preferred temperature range is about 1200°–1400°F.

In the embodiment of the invention shown in the FIGURE a mixing blade 6 is connected by a shaft 7 to a power source 8. The mixing blade is one example of the mixing means that can be used to circulate the oil 2 within the receptacle 1. Other locations for the mixing means within the bath can be equally satisfactory. However, the advantage of having the mixing blade within the sleeve as shown insures rapid movement of the heated oil away from the heating means and into the cooler majority of the oil. The object of the mixing means is that after a relatively small amount of the oil contacts the metallic element it is immediately and rapidly transferred to the relatively large amount of cooler oil. The mixing means can be energized by various means such as electricity.

Also in the embodiment of the invention shown in the FIGURE is a cooling coil 9. This cooling means is located outside of the sleeve 5 and entirely internally of the bath. Within the coil is a cooling liquid, such as chilled water, which is moved by pump 10 via connecting pipe 13 through a container 11 containing for example, a mixture of ice and water 12 or refrigeration. The heat picked up by the chilled water from oil 2 caused by heater 3 upon passing through the ice water mixture 12 is given up to melt the ice. Other means for maintaining the cooling effect are equally effective.

The purpose of the cooling means, of which cooling coil 9 and accompanying apparatus is one example, is to maintain the temperature of the liquid hydrocarbon oil 2 at a temperature substantially lower than the temperature of the metallic element as is the case in a normal quenching operation. This maintained temperature is well below the temperature of the oil 2 juxtaposed to the heated metallic element 3. Normally this maintained temperature is below 300°–400°F. A typical operative range is about 100°–200°F. This upper temperature limit is determined by the typical commercial bulk oil temperature. Preferably most of the oil 2 will be maintained at a temperature between about 100° to 150°F.

Thus the method involves heating a relatively small amount of the liquid hydrocarbon oil, which is to be tested for its thermal stability, to a temperature above the boiling point of the oil. This heating is obtained by contacting the oil with a metallic element having a suitable temperature. The temperature of the relatively small amount of oil can be as high as 1500°F and surrounding this relatively small amount of oil is a relatively large amount of oil maintained at a temperature of less than about 300°–400°F. Sufficient mixing insures that the oil at the elevated temperature is immediately transferred to the cooler oil and its heat carried away by suitable means.

Means for measuring the elevated temperature of the oil 2 in the receptacle 1 can also be included. Thus as shown in the FIGURE thermometer 14 measures the temperature of oil outside of the sleeve 5. Additional temperature measuring means can be used to measure the temperature of the oil within the sleeve 5.

Thus it can be seen that, according to the invention, data can be obtained on the effect of hot metal contacting a relatively small amount of an oil with the temperature of the relatively large amount of oil maintained at a relatively low temperature. This data is in contrast to other data wherein all of the quench oil is raised to an elevated temperature and held there for a long period of time.

The aforementioned data can be obtained by taking samples periodically from the bath. These samples are analyzed as to such properties as pentane insolubles, viscosities, and total acid number. Changes in the aforementioned properties and others known to one skilled in this art indicate degrees of degradation which are indications of the thermal stability of the oil.

Also, because the bulk temperature of the oil is controlled to well below its flash point, there is less risk of a fire. Also this lower bulk temperature reduces the amount of oil escaping to the atmosphere and minimizes cracking, both of which materially reducing air pollution.

From the foregoing description it will be appreciated that the testing apparatus of this invention very closely duplicates, in the testing laboratory, the conditions of actual commercial use of quenching oils. And that it permits an oil to be dynamically tested in days compared to the 6–8 weeks necessary when the oil is statically tested, for example, in a heated oven.

The invention claimed is:

1. A testing apparatus for use in evaluating the thermal stability of a liquid hydrocarbon oil which comprises:
  a. means for providing a bath of the liquid hydrocarbon oil to be evaluated;
  b. metallic member located entirely internally of said bath for heating said oil and means for heating said member;
  c. mixing means located internally of said bath whereby rapid movement of said oil occurs within baffling means of (d), and means for energizing the mixing means;
  d. baffling means partially enclosing the metallic member and the mixing means and the volume within the baffling means is relatively small to the total volume of the bath;
  e. cooling means located outside said baffling means and located entirely internally of a said bath for maintaining the temperature of said oil external of said baffling means at a temperature substantially lower than the temperature of said member and means for maintaining cooling effect; and
  f. said means for providing the bath, the metallic member, the mixing means, baffling means and cooling means are constructed of materials which do not chemically react with said oil; and
whereby the thermal stability of said oil can be determined.

2. Apparatus of claim 1 including also means for measuring the elevated temperature of said oil.

3. Apparatus of claim 2 wherein the metallic heating element can heat said oil to a temperature of about 1000°–1500°F and cooling means can maintain the temperature of majority of the oil at about 100°–400°F.

* * * * *